United States Patent
Johnson, II et al.

(10) Patent No.: US 10,766,013 B2
(45) Date of Patent: *Sep. 8, 2020

(54) APPARATUSES FOR MIXING OF STAGED METHANOL INJECTION

(71) Applicant: UOP LLC, Des Plaines, IL (US)

(72) Inventors: Richard A. Johnson, II, Algonquin, IL (US); Joseph A. Montalbano, Elmhurst, IL (US); John J. Senetar, Naperville, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/735,104

(22) Filed: Jan. 6, 2020

(65) Prior Publication Data

US 2020/0139327 A1    May 7, 2020

Related U.S. Application Data

(63) Continuation of application No. 15/849,529, filed on Dec. 20, 2017, now Pat. No. 10,556,214.

(51) Int. Cl.

| | | |
|---|---|---|
| *B01J 8/18* | (2006.01) | |
| *B01J 4/00* | (2006.01) | |
| *C07C 15/08* | (2006.01) | |
| *C07C 2/72* | (2006.01) | |
| *C07C 2/86* | (2006.01) | |

(52) U.S. Cl.
CPC .............. *B01J 8/1818* (2013.01); *B01J 4/002* (2013.01); *B01J 4/005* (2013.01); *C07C 2/72* (2013.01); *C07C 2/864* (2013.01); *C07C 15/08* (2013.01)

(58) Field of Classification Search
CPC ... B01J 8/18; B01J 8/1818; B01J 4/002; B01J 4/005; C07C 2/72; C07C 15/08; C07C 2/864
USPC ........................................................ 422/214
See application file for complete search history.

(56) References Cited

U.S. PATENT DOCUMENTS

| | | |
|---|---|---|
| 5,350,874 A | 9/1994 | Behrens et al. |
| 6,486,374 B1 | 11/2002 | Radcliffe et al. |
| 6,642,426 B1 | 11/2003 | Johnson et al. |
| 7,232,936 B1 | 6/2007 | Yurchak |
| 8,395,006 B2 | 3/2013 | Clark et al. |
| 8,435,452 B2 | 5/2013 | Wyatt, Jr. et al. |
| 8,877,132 B2 | 11/2014 | Johnson et al. |
| 2007/0261992 A1 | 11/2007 | Roux et al. |

(Continued)

FOREIGN PATENT DOCUMENTS

| | | |
|---|---|---|
| CN | 102316974 B | 7/2015 |
| CN | 102372585 B | 12/2015 |

(Continued)

OTHER PUBLICATIONS

International Searching Authority, International Search Report, PCT/US2018/066636, dated Mar. 21, 2019.

(Continued)

*Primary Examiner* — Huy Tram Nguyen

(57) ABSTRACT

This present disclosure relates to apparatuses for methylation of aromatics in an aromatics complex for producing a xylene isomer product. More specifically, the present disclosure relates to apparatuses for producing para-xylene by the selective methylation of toluene and/or benzene in an aromatics complex using processed toluene instead of crude toluene.

8 Claims, 1 Drawing Sheet

(56) References Cited

U.S. PATENT DOCUMENTS

2013/0280138 A1 10/2013 Johnson et al.
2013/0331631 A1 12/2013 Peterman et al.

FOREIGN PATENT DOCUMENTS

RU 2062645 C1 6/1996
RU 2147922 C1 4/2000

OTHER PUBLICATIONS

Written Opinion from PCT application No. PCT/US2018/066636, dated Mar. 5, 2019.

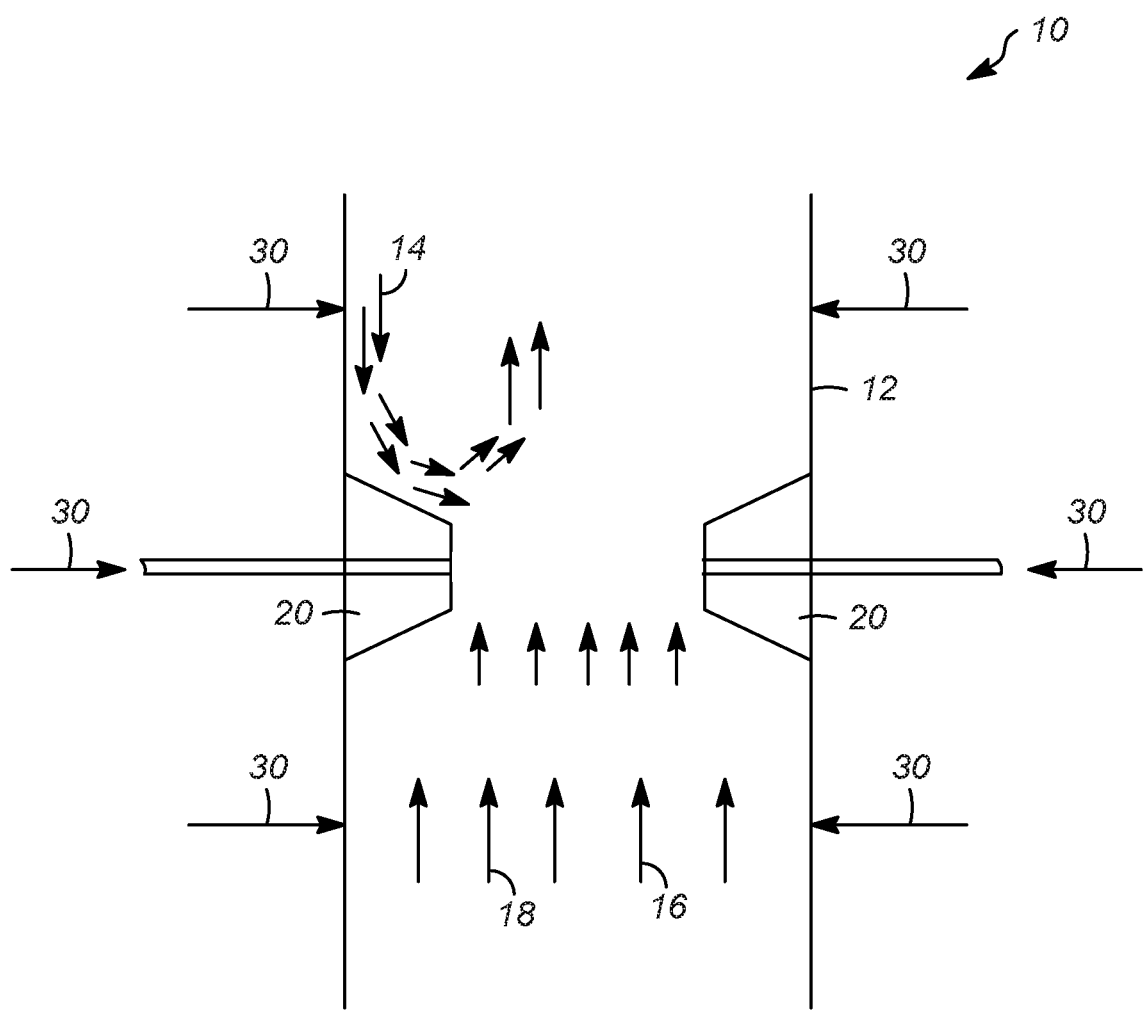

APPARATUSES FOR MIXING OF STAGED METHANOL INJECTION

RELATED APPLICATIONS

This application is a continuation of U.S. Ser. No. 15/849,529 filed on Dec. 20, 2017, now a U.S. Pat. No. 10,556,214, the entirety of which is incorporated herein by reference.

FIELD

This present disclosure relates to apparatuses for methylation of aromatics in an aromatics complex for producing a xylene isomer product. More specifically, the present disclosure relates to the use of riser slip reduction technology to improve the methanol feed and catalyst contacting which will improve the product yield rate.

BACKGROUND

Xylene isomers are produced in large volumes from petroleum as feedstocks for a variety of important industrial chemicals. The most important of the xylene isomers is para-xylene, the principal feedstock for polyester, which continues to enjoy a high growth rate from large base demand. Ortho-xylene is used to produce phthalic anhydride, which supplies high-volume but relatively mature markets. Meta-xylene is used in lesser but growing volumes for such products as plasticizers, azo dyes and wood preservers. Ethylbenzene generally is present in xylene mixtures and is occasionally recovered for styrene production, but is usually considered a less-desirable component of C8 aromatics.

Among the aromatic hydrocarbons, the overall importance of xylenes rivals that of benzene as a feedstock for industrial chemicals. Xylenes and benzene are produced from petroleum by reforming naphtha but not in sufficient volume to meet demand, thus conversion of other hydrocarbons is necessary to increase the yield of xylenes and benzene. Often toluene is de-alkylated to produce benzene or selectively disproportionated to yield benzene and C8 aromatics from which the individual xylene isomers are recovered.

Methylation of toluene or benzene with oxygenates such as methanol has been proposed as a pathway to make xylene and to increase methyl to phenyl ratio in the aromatic complex to maximize xylene production. For the toluene methylation process there is a yield advantage to add methanol at various locations above the main feed injection point. The reactor is a transport riser style with the feed and catalyst flowing co-currently up the riser. In this riser style and operating conditions, there will be a catalyst velocity gradient in the radial direction in which some catalyst will slow down and begin to fall down along the riser wall. In addition, the high upward momentum of catalyst away from the wall does not allow the methanol injection from the side of riser to penetrate and mix into the main flow of catalyst. This decreases the methanol injection's effectiveness, and thus yield improvements may not be realized.

Accordingly, it is desirable to provide improved apparatuses for methylation of aromatic compounds such as toluene and benzene in an aromatics complex. Furthermore, other desirable features and characteristics of the present subject matter will become apparent from the subsequent detailed description of the subject matter and the appended claims, taken in conjunction with the accompanying drawing and this background of the subject matter.

SUMMARY

The present subject matter relates to apparatuses for toluene and/or benzene methylation in an aromatics complex for producing xylene isomer. More specifically, the present disclosure relates to apparatuses for toluene methylation wherein the use of riser slip reduction technology to improve the methanol feed and catalyst contacting, which will improve the product yield rate.

In the foregoing, all temperatures are set forth in degrees Celsius and all parts and percentages are by weight, unless otherwise indicated. Other objects, advantages and applications of the present invention will become apparent to those skilled in the art from the following detailed description and drawing. Additional objects, advantages and novel features of the examples will be set forth in part in the description which follows, and in part will become apparent to those skilled in the art upon examination of the following description and the accompanying drawing or may be learned by production or operation of the examples. The objects and advantages of the concepts may be realized and attained by means of the methodologies, instrumentalities and combinations particularly pointed out in the appended claims.

BRIEF DESCRIPTION OF THE DRAWING

The FIGURE illustrates a cross-sectional view of an apparatus for toluene methylation demonstrating the use of riser slip reduction technology to improve the methanol feed and catalyst contacting.

DETAILED DESCRIPTION

The following detailed description is merely exemplary in nature and is not intended to limit the application and uses of the embodiment described. Furthermore, there is no intention to be bound by any theory presented in the preceding background or the following detailed description.

The description of the apparatus of this invention is presented with reference to the attached FIGURE. The FIGURE is a simplified diagram of the preferred embodiment of this invention and is not intended as an undue limitation on the generally broad scope of the description provided herein and the appended claims. Certain hardware such as valves, pumps, compressors, heat exchangers, instrumentation and controls, have been omitted as not essential to a clear understanding of the invention. The use and application of this hardware is well within the skill of the art.

The various embodiments described herein relate to apparatuses for toluene and/or benzene methylation in an aromatics complex for producing xylene isomer. As shown in the FIGURE, an apparatus 10 comprises a riser 12, which is a toluene methylation stage methanol injection riser reactor. In the riser, there is falling catalyst 14 that falls downward on the edges of the riser 12 and a majority of the catalyst 16 that is rising within the riser 12 along with vapor 18. The riser 12 includes at least one riser slip reduction technology, hereinafter referred to as a baffle 20.

In one embodiment, the baffles 20 are positioned symmetrically around the circumference of the riser 12. In another embodiment, the baffles 20 are arranged non-symmetrically. In some embodiments, the baffles 20 can cover less of the circumference, if desired. For example, typically at least about 30% of the circumference is covered with baffles 20, or at least about 40%, or at least about 50%, or at least about 60%, or at least about 70%, or at least about 80%, or at least about 90%, or at least about 95%.

The baffles 20 extend inward from the wall a distance up to about 25% of the radius of the riser, typically in the range of about 10% to about 30%. The length depends in part on the radius of the riser 12 and the angle from the wall. The angle of the baffles 20 ranges from about 5° to about 80° from vertical. The baffles 20 may be coupled with additional lining to ensure the erosion resistance.

The riser 12 desirably has at least two rows of baffles 20 along its length so that the core-annulus structure does not return to its original state as it flows up the riser 12. However, if there are too many rows of baffles 20, the catalyst-laden vapors flowing upward will simply bypass the baffles 20 altogether, effectively reducing the diameter of the riser 12.

A number of factors can be considered in determining the appropriate angle for the baffles 20 in a particular riser 12. One consideration is mixing, with larger angles producing greater mixing. Another factor is the amount of erosion, which is greater for larger angles. Still another factor is the pressure drop generated by the baffles 20, which is greater for baffles 20 having larger angles than for those with smaller angles. In addition, the effect of thermal differential growth should be evaluated. When the angle is about 90°, the wall and the baffle might expand at different rates, which could potentially lead to cracking. With smaller angles, such as about 10° to about 45°, the relatively long inclined support plate provides a longer path for heat transfer. This minimizes the thermal differential growth of the baffle, especially under transient conditions, such as start-up or shut-down.

The baffles 20 are made of a material having sufficient erosion- and temperature-resistance to withstand the riser conditions. Suitable materials include metal plates, such as stainless steel plates, covered with ceramic on at least the front face facing the upward flow to prevent erosion. The back side away from the flow can be covered with abrasion-resistant refractory. Alternatively, both sides can be covered with ceramic.

The riser 12 also includes a plurality of distributors 30 for the delivery of methanol into the riser 12. In one embodiment, the distributors 30 may be located above the baffles. In another embodiment, the distributors 30 may be located through the baffle 20, allowing for the distribution of methanol to enter the inside of the riser 12 at a different radial position. In yet another embodiment, the distributors 30 may be located beneath the baffles 20. The distributors 30 deliver methanol to the riser 12.

While the invention has been described with what are presently considered the preferred embodiments, it is to be understood that the invention is not limited to the disclosed embodiments, but it is intended to cover various modifications and equivalent arrangements included within the scope of the appended claims.

Specific Embodiments

While the following is described in conjunction with specific embodiments, it will be understood that this description is intended to illustrate and not limit the scope of the preceding description and the appended claims.

A first embodiment of the invention is an apparatus, comprising a cylindrical riser comprising an outer wall and an inner wall, wherein the inner wall comprises at least one baffle affixed to the inner wall extending inward into the riser, a bottom opening, and upper opening, and at least one distributor. An embodiment of the invention is one, any or all of prior embodiments in this paragraph up through the first embodiment in this paragraph, wherein the baffle extends around the entire inner wall of the riser reactor. An embodiment of the invention is one, any or all of prior embodiments in this paragraph up through the first embodiment in this paragraph, wherein the distributor is located above the baffles. An embodiment of the invention is one, any or all of prior embodiments in this paragraph up through the first embodiment in this paragraph, wherein the distributor is located below the baffles. An embodiment of the invention is one, any or all of prior embodiments in this paragraph up through the first embodiment in this paragraph, wherein the distributor extends through the baffle and into a different radial location within the riser reactor. An embodiment of the invention is one, any or all of prior embodiments in this paragraph up through the first embodiment in this paragraph, wherein the distributor is angled from 30 degrees to 120 degrees relative to the riser wall. An embodiment of the invention is one, any or all of prior embodiments in this paragraph up through the first embodiment in this paragraph, wherein the distributors are located at two different axial locations within the riser reactor. An embodiment of the invention is one, any or all of prior embodiments in this paragraph up through the first embodiment in this paragraph, wherein there are at least two rows of baffles. An embodiment of the invention is one, any or all of prior embodiments in this paragraph up through the first embodiment in this paragraph, wherein the baffles are arranged symmetrically around the wall of the riser. An embodiment of the invention is one, any or all of prior embodiments in this paragraph up through the first embodiment in this paragraph, wherein baffles cover substantially the entire circumference of the riser. An embodiment of the invention is one, any or all of prior embodiments in this paragraph up through the first embodiment in this paragraph, wherein the riser reactor is a toluene methylation riser reactor. A apparatus, comprising a cylindrical riser comprising an outer wall and an inner wall, wherein the inner wall comprises at least one baffle affixed to the inner wall extending inward into the riser covering substantially the entire circumference of the riser, a bottom opening, and upper opening, and two distributors located above the baffles. An embodiment of the invention is one, any or all of prior embodiments in this paragraph up through the first embodiment in this paragraph, wherein the distributors extend through the baffle and into a different radial location within the riser reactor. An embodiment of the invention is one, any or all of prior embodiments in this paragraph up through the first embodiment in this paragraph, wherein the distributor is angled from 30 degrees to 120 degrees relative to the riser wall. An embodiment of the invention is one, any or all of prior embodiments in this paragraph up through the first embodiment in this paragraph, wherein there are at least two rows of baffles. An embodiment of the invention is one, any or all of prior embodiments in this paragraph up through the first embodiment in this paragraph, wherein the baffles are arranged symmetrically around the wall of the riser. An embodiment of the invention is one, any or all of prior embodiments in this paragraph up through the first embodiment in this paragraph, wherein the riser reactor is a toluene methylation riser reactor.

A second embodiment of the invention is an apparatus, comprising a cylindrical riser comprising an outer wall and an inner wall, wherein the inner wall comprises at least one baffle affixed to the inner wall extending inward into the riser covering substantially the entire circumference of the riser, a bottom opening, and upper opening, and two distributors located below the baffles. An embodiment of the invention is one, any or all of prior embodiments in this paragraph up through the second embodiment in this paragraph, wherein the distributors extend through the baffle and into a different radial location within the riser reactor. An embodiment of the invention is one, any or all of prior embodiments in this paragraph up through the second embodiment in this paragraph, wherein the distributor is angled from 30 degrees to 120 degrees relative to the riser wall.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims. In the foregoing, all temperatures are set forth in degrees Celsius and, all parts and percentages are by weight, unless otherwise indicated.

The invention claimed is:

1. A riser reactor, comprising:
    a cylindrical riser comprising an outer wall and an inner wall;
    at least one baffle affixed to the inner wall extending into the riser; and
    at least one distributor configured to inject methanol into the riser, wherein the at least one distributor is located above the at least one baffle, below the at least one baffle, extends through the at least one baffle and into a different radial location within the riser reactor, or a combination thereof.

2. The riser reactor of claim 1, wherein the at least one baffle extends around the entire inner wall of the riser reactor.

3. The riser reactor of claim 1, wherein the at least one distributor is angled from 30 degrees to 120 degrees relative to the inner wall.

4. The riser reactor of claim 1, further comprising a second distributor, wherein the distributors are located at two different axial locations within the riser reactor.

5. The riser reactor of claim 1, wherein there are at least two rows of baffles.

6. The riser reactor of claim 1, further comprising a plurality of baffles and wherein the baffles are arranged symmetrically around the inner wall of the riser.

7. The riser reactor of claim 1, further comprising a plurality of baffles and wherein baffles cover substantially a circumference of the riser.

8. The riser reactor of claim 1, wherein the riser reactor is a toluene methylation riser reactor.

* * * * *